(12) United States Patent
Forohar et al.

(10) Patent No.: US 6,218,554 B1
(45) Date of Patent: Apr. 17, 2001

(54) SUBSTITUTED CYCLOTETRAPHOSPHAZENE COMPOUND AND METHOD OF PRODUCING THE SAME

(75) Inventors: Farhad Forohar, Flanders; Paritosh R. Dave, Bridgewater; Sury Iyer, Randolph, all of NJ (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/663,108

(22) Filed: Sep. 15, 2000

Related U.S. Application Data

(63) Continuation-in-part of application No. 09/639,268, filed on Aug. 15, 2000.

(51) Int. Cl.[7] .............................. C07F 9/02; C06B 49/00; C06B 43/00
(52) U.S. Cl. .............................. 552/3; 568/12; 149/108.6; 149/121
(58) Field of Search .................................. 568/12; 552/3; 149/108.6, 121

(56) References Cited

PUBLICATIONS

Database Caplus on STN, Acc. No. 1981:408685, Heitsch et al., 'Fire retardant textiles—cotton treated with amidophosphazene.' Org. Coat. Plast. Chem. (1979), 41, pp. 97–102 (abstract), 1981.*

* cited by examiner

*Primary Examiner*—Johann Richter
*Assistant Examiner*—Brian J. Davis
(74) *Attorney, Agent, or Firm*—Robert Beam; John F. Moran; Michael C. Sachs

(57) ABSTRACT

A novel cyclotetraphosphazene compound, 1,5-diamino-1,3,3,5,7,7-hexaazidocyclotetraphosphazene, is disclosed which has application as an energetic compound. Also disclosed is a method of preparing the compound.

3 Claims, No Drawings

SUBSTITUTED CYCLOTETRAPHOSPHAZENE COMPOUND AND METHOD OF PRODUCING THE SAME

CROSS REFERENCE TO RELATED APPLICATIONS

The present application is a continuation-in-part of U.S. patent application Ser. No. 09/639,268, filed Aug. 15, 2000, now allowed.

STATEMENT REGARDING FEDERALLY SPONSORED RESEARCH OR DEVELOPMENT

The invention described herein may be made, used, or licensed by or for the United States Government for Governmental purposes without the payment of any royalties thereon or therefor.

BACKGROUND OF THE INVENTION

1. Field of the Invention

The present invention relates to a novel cyclotetraphosphazene compound and a method of producing the same. In particular, the present invention relates to 1,5-diamino-1,3,3,5,7,7-hexaazidocyclotetraphosphazene, which has shown to be useful as an energetic composition.

2. Description of Related Art

Many energetic compositions are environmentally objectionable. As an example, prior art percussion primers typically use lead azide, lead styphnate, antimony sulfide, barium nitrate, mercury fulmanate and other materials containing heavy metals that are known to contribute to environmental pollution during manufacturing and use. Firing of small arms, especially in indoor firing ranges, releases clouds of hazardous gases in addition to increased contamination of the soil and ground water.

The need for alternative energetic compositions that are more environmentally friendly has been felt for some time, and several attempts have been made to provide such a compound.

U.S. Pat. No. 5,717,159 issued to Dixon, Martin, and Thompson on Feb. 10, 1998. This reference is entitled Lead-Free Percussion Primer Mixes Based on Metastable Interstitial Composite (MIC) Technology, and discloses a mixture of aluminum powder having an outer coating of aluminum oxide and either molybdenum trioxide or polytetrafluoroethylene.

U.S. Pat. No. 5,993,577 issued to Erickson, Melberg and Sandstrom on Nov. 30, 1999. This reference is entitled Lead-Free, Heavy-Metal-Free Rim-Fire Priming Composition, and discloses a combination of diazodinitrophenol, tetracene, ground glass, and a lead-free, heavy-metal-free oxidizer, together with a binder and a dye.

Cyclotriphosphazenes have been reported as energetic compounds in *Novel Spiro Substituted Cyclotriphosphazenes Incorporating Ethylenedinitramine Units*, Dave, et al., Phosphorus, Sulfur, and Silicon, 1994, vol. 90, pp. 175–184, and in *Synthesis Of Ethylenedinitramine Deriatives Of Fluorocyclotriphosphazenes*, Forohar, et al., Phosphorus, Sulfur, and Silicon, 1995, vol. 101, pp. 161–166.

BRIEF SUMMARY OF THE INVENTION

Objects of the Invention

It is an object of the present invention to provide an environmentally friendly energetic compound.

The other objects, features and advantages of the present invention will become more apparent in light of the following detailed description of the preferred embodiment thereof.

SUMMARY OF THE INVENTION

According to the present invention, a novel compound, 1,5-diamino-1,3,3,5,7,7-hexaazidocyclotetraphosphazene, is disclosed.

According to another embodiment of the present invention, there is disclosed a novel energetic composition comprising 1,5-diamino-1,3,3,5,7,7-hexaazidocyclotetraphosphazene.

According to a still further embodiment of the present invention, there is disclosed a method of preparation of 1,5-diamino-1,3,3,5,7,7-hexaazidocyclotetraphosphazene, which method comprises the steps of:

a. reacting a quantity of octachlorocyclotetraphosphazene with ammonium hydroxide in ether to produce isomers of diaminohexachlorocyclotetraphosphazene;

b. isolating 1,5-diamino-1,3,3,5,7,7-hexachlorocyclotetraphosphazene from the reaction product of step (a);

c. reacting the 1,5-diamino-1,3,3,5,7,7-hexachlorocyclotetraphosphazene with sodium azide in acetone to produce 1,5-diamino-1,3,3,5,7,7-hexaazidocyclotetraphosphazene.

DETAILED DESCRIPTION OF THE INVENTION

Phosphazenes are phosphorous-nitrogen ring compounds which have two substituents attached to each phosphorous atom. These substituents can be manipulated to place a variety of different groups on the ring system. Two major types of phosphazenes appear to have commercial use. The first class includes six membered ring cyclotriphosphazenes such as hexachlorocyclotriphosphazene. The second class includes eight membered ring cyclotetraphosphazenes such as octachlorocyclotetraphosphazene.

The present invention comprises a novel cyclotetraphosphazene derived from octachlorocyclotetraphosphazene, which is commercially available from Phosphazene Custom Synthesis, Inc., 2820 East College Avenue, Suite N, State College, Pa. 16801. The novel compound of the present invention, 1,5-diamino-1,3,3,5,7,7-hexaazidocyclotetraphosphazene, was synthesized and identified as a new class of environmentally friendly energetic compositions. It has demonstrated positive experimental results for such application.

This novel compound of the present invention, 1,5-diamino-1,3,3,5,7,7-hexaazidocyclotetraphosphazene, was synthesized from octachlorocyclotetraphosphazene in the following manner. First, a quantity of octachlorocyclotetraphosphazene was reacted with ammonium hydroxide in ether to produce isomers of diaminohexachlorocyclotetraphosphazene. This reaction has been reported in the literature. See, J. K. Fincham, R. A. Shaw, "Phosphorous-Nitrogen Compounds. Part 62". *Phosphorous, Sulfur, and Silicon*, 1990, Vol. 47, p. 109. Then, after isolating 1,5-diamino-1,3,3,5,7,7-hexachlorocyclotetraphosphazene from the reaction products of the first step, the 1,5-diamino-1,3,3,5,7,7-hexachlorocyclotetraphosphazene was reacted with sodium azide in acetone to produce 1,5-diamino-1,3,3,5,7,7-hexaazidocyclotetraphosphazene, which was then obtained from solution.

Differential Scanning Calorimetry (DSC) indicated that the novel compound decomposes violently at two hundred thirty-four degrees Celsius (234° C.).

EXAMPLE 1

Synthesis of 1,5-diamino-1,3,3,5,7,7-hexachlorocyclotetraphosphazene

A two-liter four-neck round-bottom flask was equipped with a condenser, an addition funnel, a mechanical stirrer, and a stopcock. One hundred and fifty grams (150 g.) of sodium sulfate, five hundred milliliters (500 ml) of ethyl ether, and eleven and two-tenths grams (11.2 g.) of octachlorocyclotetraphosphazene were added to the round bottom flask. An ice bath was placed under the flask and the mixture was stirred vigorously by the mechanical stirrer. Seven milliliters (7 ml) of reagent grade (17M) ammonium hydroxide in a further one hundred milliliters (100 ml) of ethyl ether was transferred into the flask by way of the addition funnel, and slowly added to the reaction mixture over a two hour (2 hour) period. After the addition was completed, the mixture was stirred at ice bath temperature for an additional one-half hour (½ hour).

The reaction mixture was then filtered to remove the sodium sulfate and the ammonium chloride by-product. The resulting clear solution obtained after filtration was subjected to a rotary evaporator to remove the solvent. A white solid crude product was obtained after solvent removal, and the solvent could, in principle, be recycled.

The white solid was ground and crushed to a finer particle size and stirred in three hundred milliliters (300 ml) of petroleum ether, then recovered by filtration. About four hundred milliliters of cyclohexane was added to the solid and the resulting suspension was refluxed for thirty minutes (30 min.) and quickly filtered. Three and six-tenths grams (3.6 g.) of a white solid was collected, representing a yield of thirty-five and one-tenth percent (35.1%). Based upon the measured melting point of two hundred and five to two hundred and seven degrees Celsius (205–207° C.), this was 1,5-diamino-1,3,3,5,7,7-hexachlorocyclotetraphosphazene.

EXAMPLE 2

Synthesis of 1,5-diamino-1,3,3,5,7,7-hexaazidocyclotetraphosphazene

One gram (1.0 g.) of 1,5-diamino-1,3,3,5,7,7-hexachlorocyclotetraphosphazene, four grams (4.0 g.) of sodium azide, and one hundred and twenty milliliters (120 ml) of acetone were placed into a two hundred and fifty milliliter (250 ml) round bottom flask containing a magnetic stirring bar. The resulting suspension was stirred at room temperature for twenty hours (20 hours). The suspension was then filtered to remove the excess sodium azide and the sodium chloride by-product.

The acetone solution was carefully concentrated by rotary evaporation to get a slightly yellow oil. The oil was extracted with one hundred milliliters (100 ml) of ethyl ether and twenty-five milliliters (25 ml) of water. The organic solution was dried over sodium sulfate, filtered, and concentrated to obtain eight-tenths of a gram (0.8 g.) of 1,5-diamino-1,3,3,5,7,7-hexaazidocyclotetraphosphazene as a colorless oil, representing a yield of about seventy-three percent (73%).

The colorless oil obtained in this manner had a decomposition temperature of two hundred and thirty-four degrees Celsius (234° C.). The oil was confirmed to be 1,5-diamino-1,3,3,5,7,7-hexaazidocyclotetraphosphazene by Phosphorous Nuclear Magnetic Resonance ($^{31}P$ NMR), which showed peaks at $\delta 2.45$ (t), and $\delta -6.01$ (t). The Infrared Absorption Spectra of the oil (neat, NaCl plate) showed bands of absorption at 2144 $cm^{-1}$ ($N_3$) and 3344 $cm^{-1}$ ($NH_2$).

The oil obtained was highly impact and friction sensitive. One possible application of the oil would be to dissolve it in a solvent such as acetone and apply it as a coating material to powerful energetic materials such as hexanitrohexaazaisowurtzitane (Cl-20) or 1,3,3-trinitroazetidine (TNAZ). Such a coated energetic material could potentially generate powerful primary explosives.

A comparison of the molecular formula of lead azide, $Pb(N_3)_2$, and the novel compound of the present invention $(P_4N_4)(N_3)_6(NH_2)_2$, indicates that the novel compound of the present invention contain a greater number of energetic moieties than lead azide. Lead azide has only six nitrogen atoms per molecule while the novel compound of the present invention has 24 nitrogen atoms. Assuming total conversion of nitrogen atoms to nitrogen gas, a single molecule of the novel compound of the present invention can generate 3.6 times more nitrogen gas than each molecule of lead azide. In terms of the mass balance of each molecule, lead azide contains seventy-one percent (71%) of the non-energetic heavy-metal lead and only twenty-one percent (21%) nitrogen. The novel compound of the present invention, by comparison, contains seventy-two percent (72%) nitrogen, twenty-seven percent (27%) phosphorous, and one percent (1%) hydrogen. This comparison indicates that the expandable gases generated by the decomposition of the novel compound of the present invention are superior to those generated by lead azide.

Other features, and specific embodiments of this information will become readily apparent to those exercising ordinary skill in the art after reading the foregoing disclosures. These specific embodiments are within the scope of the claimed subject matter unless otherwise expressly indicated to the contrary. Moreover, while specific embodiments of this invention have been described in considerable detail, variations and modifications of these embodiments can be effected without departing from the spirit and scope of this invention as disclosed and claimed.

What is claimed is:

1. 1,5-diamino-1,3,3,5,7,7-hexaazidocyclotetraphosphazene.

2. An energetic composition comprising 1,5-diamino-1,3,3,5,7,7-hexaazidocyclotetraphosphazene.

3. A method of preparation of 1,5-diamino-1,3,3,5,7,7-hexaazidocyclotetraphosphazene, which method comprises the steps of:

a. reacting a quantity of octachlorocyclotetraphosphazene with ammonium hydroxide in ether to produce isomers of diaminohexachlorocyclotetraphosphazene;

b. isolating 1,5-diamino-1,3,3,5,7,7-hexachlorocyclotetraphosphazene from the reaction product of step (a);

c. reacting the 1,5-diamino-1,3,3,5,7,7-hexachlorocyclotetraphosphazene with sodium azide in acetone to produce 1,5-diamino-1,3,3,5,7,7-hexaazidocyclotetraphosphazene.

\* \* \* \* \*